(12) United States Patent
Nicholas et al.

(10) Patent No.: US 8,889,939 B2
(45) Date of Patent: Nov. 18, 2014

(54) DEHYDROCYCLODIMERIZATION USING UZM-44 ALUMINOSILICATE ZEOLITE

(71) Applicant: UOP LLC, Des Plaines, IL (US)

(72) Inventors: Christopher P. Nicholas, Evanston, IL (US); Mark A. Miller, Niles, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/094,060

(22) Filed: Dec. 2, 2013

(65) Prior Publication Data

US 2014/0163279 A1    Jun. 12, 2014

Related U.S. Application Data

(60) Provisional application No. 61/736,333, filed on Dec. 12, 2012.

(51) Int. Cl.
   *C07C 2/76*    (2006.01)

(52) U.S. Cl.
   CPC ..................................... *C07C 2/76* (2013.01)
   USPC .......................................... 585/418; 585/407

(58) Field of Classification Search
   CPC ......................................................... C07C 2/76
   USPC ................................................. 585/418, 407
   See application file for complete search history.

(56) References Cited

U.S. PATENT DOCUMENTS

| | | | |
|---|---|---|---|
| 2,620,314 A | 12/1952 | Hoekstra | |
| 2,948,675 A | 8/1960 | Case et al. | |
| 3,146,188 A | 8/1964 | Gossett | |
| 3,227,645 A | 1/1966 | Frumkin et al. | |
| 3,658,695 A | 4/1972 | VanPool | |
| 3,839,187 A | 10/1974 | Vanvenrooy | |
| 4,197,192 A | 4/1980 | Gould | |
| 4,310,440 A | 1/1982 | Wilson et al. | |
| 4,354,928 A | 10/1982 | Audeh et al. | |
| 4,440,871 A | 4/1984 | Lok et al. | |
| 4,478,705 A | 10/1984 | Ganguli | |
| 4,483,691 A | 11/1984 | McShea, III et al. | |
| 4,645,589 A | 2/1987 | Krambeck et al. | |
| 4,870,222 A | 9/1989 | Bakas et al. | |
| 4,946,812 A * | 8/1990 | Shum | 502/61 |
| 5,157,196 A | 10/1992 | Crossland et al. | |
| 5,157,197 A | 10/1992 | Cooper et al. | |
| 5,961,756 A | 10/1999 | Freel et al. | |
| 6,136,290 A | 10/2000 | Benazzi et al. | |
| 6,239,057 B1 | 5/2001 | Ichikawa et al. | |
| 6,426,442 B1 | 7/2002 | Ichikawa et al. | |
| 6,514,479 B1 | 2/2003 | Merlen et al. | |
| 6,613,302 B1 | 9/2003 | Moscoso et al. | |
| 6,627,781 B1 | 9/2003 | Briot et al. | |
| 6,740,788 B1 | 5/2004 | Maher et al. | |
| 6,756,030 B1 | 6/2004 | Rohde et al. | |
| 6,776,975 B2 | 8/2004 | Wilson et al. | |
| 7,374,662 B2 | 5/2008 | Duplan et al. | |
| 7,419,931 B2 | 9/2008 | Serra et al. | |
| 7,575,737 B1 | 8/2009 | Miller et al. | |
| 7,615,143 B2 | 11/2009 | Chen et al. | |
| 7,629,499 B2 | 12/2009 | Serra Alfaro et al. | |
| 7,638,667 B2 | 12/2009 | Jan et al. | |
| 7,687,423 B2 | 3/2010 | Moscoso et al. | |
| 7,713,513 B2 | 5/2010 | Jan et al. | |
| 7,915,469 B2 | 3/2011 | Miller et al. | |
| 7,982,083 B2 | 7/2011 | Guillon et al. | |
| 8,048,403 B2 | 11/2011 | Miller et al. | |
| 8,058,495 B2 | 11/2011 | Jan et al. | |
| 8,134,037 B2 | 3/2012 | Bogdan et al. | |
| 8,178,740 B2 | 5/2012 | Nicholas et al. | |
| 8,183,172 B2 | 5/2012 | Guillon et al. | |
| 8,263,032 B2 | 9/2012 | Andersen et al. | |
| 8,398,955 B2 | 3/2013 | Lai et al. | |
| 8,461,405 B2 | 6/2013 | Sanchez et al. | |
| 8,609,910 B1 | 12/2013 | Nicholas et al. | |
| 8,609,911 B1 | 12/2013 | Nicholas et al. | |

(Continued)

FOREIGN PATENT DOCUMENTS

| | | |
|---|---|---|
| CA | 2268803 A1 | 4/1998 |
| CN | 102040459 | 5/2011 |

(Continued)

OTHER PUBLICATIONS

Hong et al., "Synthesis, Structure Solution, Characterization, and Catalytic Properties of TNU-10: A High-Silica Zeolite with the STI Topology", J. Am. Chem Society, 2004, vol. 126, pp. 5718-5826.
Gramm et al., "Complex zeolite structure solved by combining powder diffraction and electron microscopy", Nature, 2006, vol. 444, pp. 79-81.
Baerlocher et al., "Structure of Polycrystalline Zeolite Catalyst IM-5 Solved by Enhanced Charge Flipping", Science, 2007, vol. 315, pp. 1113-1116.
Rietveld, "A Profile Refinement Method for Nuclear and Magnetic Structures", Journal of Applied Crystallography, 1969, vol. 2, pp. 65-71.
Brunauer et al., "Adsorption of Gases in Multimolecular Layers", J. Am. Chem Society, 1938, vol. 60, pp. 309-319.
Portilla et al., "Structure-reactivity relationship for aromatics transalkylation and isomerization process with TNU-9, MCM-22 and ZSM-5 zeolites, and their industrial implications", Applied Catalysis A: General, 2011, vol. 393, n 1-2, pp. 257-268.

(Continued)

*Primary Examiner* — Thuan D Dang
(74) *Attorney, Agent, or Firm* — Maryann Maas

(57) ABSTRACT

A process for dehydrocyclodimerization using a catalytic composite comprising at least one of a new family of aluminosilicate zeolites designated UZM-44 has been developed. These zeolites are represented by the empirical formula.

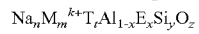

$Na_nM_m^{k+}T_rAl_{1-x}E_xSi_yO_z$ where "n" is the mole ratio of Na to (Al+E), M represents a metal or metals from zine, Group 1, Group 2, Group 3 and or the lanthanide series of the periodic table, "m" is the mole ratio of M to (Al+E), "k" is the average charge of the metal or metals M, T is the organic structure directing agent or agents, and E is a framework element such as gallium. UZM-44 has catalytic properties for carrying processes involving contacting at least one aliphatic hydrocarbon having from 2 to about 6 carbon atoms per molecule with the UZM-44 to produce at least one aromatic hydrocarbon.

18 Claims, 3 Drawing Sheets

(56) References Cited

U.S. PATENT DOCUMENTS

| | | |
|---|---|---|
| 8,609,919 B1 | 12/2013 | Nicholas et al. |
| 8,609,920 B1 | 12/2013 | Miller et al. |
| 8,609,921 B1 | 12/2013 | Nicholas et al. |
| 8,618,343 B1 | 12/2013 | Nicholas et al. |
| 8,623,321 B1 | 1/2014 | Miller et al. |
| 8,633,344 B2 | 1/2014 | Nicholas et al. |
| 8,642,823 B2 | 2/2014 | Nicholas et al. |
| 2008/0179221 A1 | 7/2008 | Nguyen et al. |
| 2010/0145123 A1 | 6/2010 | Nicholas et al. |
| 2010/0298117 A1 | 11/2010 | Levin et al. |
| 2011/0174692 A1 | 7/2011 | Negiz et al. |
| 2011/0178354 A1 | 7/2011 | Negiz et al. |
| 2012/0024754 A1 | 2/2012 | Chen et al. |
| 2012/0029256 A1 | 2/2012 | Chen et al. |
| 2012/0121486 A1 | 5/2012 | Collier et al. |

FOREIGN PATENT DOCUMENTS

| | | |
|---|---|---|
| DE | 69710612 | 11/2002 |
| GB | 682387 | 11/1952 |
| GB | 915601 | 1/1963 |
| JP | 11253810 | 9/1999 |
| JP | 4595106 | 12/2010 |
| KR | 480229 | 3/2005 |
| KR | 2011047178 | 5/2011 |
| KR | 2012023156 | 3/2012 |
| KR | 1174099 | 8/2012 |
| KR | 2012091865 | 8/2012 |
| WO | 9817581 | 4/1998 |
| WO | 2012027034 A2 | 3/2012 |

OTHER PUBLICATIONS

Serra et al., "A rational design of alkyl-aromatics dealkylation-transalkylation catalysts using C8 and C9 alkyl-aromatics as reactants", Journal of Catalysis, 2004, vol. 227, n 2, pp. 459-469.

Cejka et al., "Novel zeolites in transformation of aromatic hydrocarbons", King Fahd University of Petroleum and Minerals—18th Annual Saudi-Japan Symposium on Catalysts in Petroleum Refining and Petrochemicals, Nov. 2008, pp. 117-126, Publisher: King Fahd Univ. of Petroleum and Minerals Res. Inst.

Bleken et al., "Conversion of methanol over 10-ring zeolites with differing volumes at channel intersections: Comparison of TNU-9, IM-5, ZSM-11 and ZSM-5w", Physical Chemistry Chemical Physics, 2011, vol. 13, n 7, pp. 2539-2549.

Odedairo et al., "Toluene disproportionation and methylation over zeolites TNU-9, SSZ-33, ZSM-5, and mordenite using different reactor systems", Industrial and Engineering Chemistry Research, 2011, vol. 50, n 6, pp. 3169-3183.

Corma et al., "IM-5: A highly thermal and hydrothermal shape-selective cracking zeolite", Journal of Catalysis, 2002, vol. 206, n 1, pp. 125-133.

Jae et al., "Production of green aromatics from catalytic fast pyrolysis of lignocellulosic biomass", 11AIChE—2011 AIChE Annual Meeting, Conference Proceedings, Oct. 16-21, 2011, Publisher: American Institute of Chemical Engineers.

Jae et al., "Investigation into the shape selectivity of zeolite catalysts for biomass conversion", Journal of Catalysis, 2011, vol. 279, n 2, pp. 257-268.

Tukur et al., "Comparison studies of xylene isomerization and disproportionation reactions between SSZ-33, TNU-9, mordenite and ZSM-5 zeolite catalysts", Chemical Engineering Journal, vol. 166, n 1, pp. 348-357, Jan. 1, 2011.

Hong et al., "Synthesis, crystal structure, characterization, and catalytic properties of TNU-9", Journal of the American Chemical Society, 2007, vol. 129, n 35, pp. 10870-10885.

Corma et al., "Determination of the pore topology of zeolite IM-5 by means of catalytic test reactions and hydrocarbon adsorption measurements", Journal of Catalysis, 2000, vol. 189, n 2, pp. 382-394.

Lee et al., "Synthesis, characterization, and catalytic properties of zeolites IM-5 and NU-88", Journal of Catalysis, 2003, vol. 215, n 1, pp. 151-170.

Palomares et al., "Co-exchanged IM5, a stable zeolite for the selective catalytic reduction of NO in the presence of water and SO2", Industrial and Engineering Chemistry Research, 2003, vol. 42, n 8, pp. 1538-1542.

He et al., "A theoretical study of the stability of $Cu^{2+}$ ion in IM-5 zeolite and the interaction of Cu-IM-5 with NO", Microporous and Mesoporous Materials, 2009, vol. 121, n 1-3, pp. 95-102.

Liu et al., "Synthesis of Mo/TNU-9 (TNU-9 Taejon National University No. 9) catalyst and its catalytic performance in methane non-oxidative aromatization", Energy, 2011, vol. 36, n 3, pp. 1582-1589.

Liu et al., "Synthesis of Mo/IM-5 catalyst and its catalytic behavior in methane non-oxidative aromatization", Fuel, 2011, vol. 90, n 4, pp. 1515-1521.

Li et al., "Deep oxidative desulfurization of fuels in redox ionic liquids based on iron chloride", Green Chemistry, 2009, vol. 11, pp. 810-815.

Feng et al., "Application of phosphate ionic liquids in deep desulfurization of fuel", Petrochemical Technology, 2006, vol. 35, pp. 272-276.

Nie et al., "N, N-dialkylimidazolium dialkylphosphate ionic liquids: Their extractive performance for thiopene series compounds from fuel oils versus the length of alkyl group", Fuel Processing Technology, 2008, vol. 89, pp. 978-983.

U.S. Appl. No. 13/714,486, filed Dec. 14, 2012, Nicholas et al.
U.S. Appl. No. 13/714,539, filed Dec. 14, 2012, Nicholas et al.
U.S. Appl. No. 13/714,504, filed Dec. 14, 2012, Nicholas et al.
U.S. Appl. No. 14/102,524, filed Dec. 11, 2013, Voskoboynikov et al.
U.S. Appl. No. 14/105,993, filed Dec. 11, 2013, Voskoboynikov et al.
U.S. Appl. No. 14/102,849, filed Dec. 11, 2013, Voskoboynikov et al.
U.S. Appl. No. 14/102,523, filed Dec. 11, 2013, Nicholas et al.

* cited by examiner

DEHYDROCYCLODIMERIZATION USING UZM-44 ALUMINOSILICATE ZEOLITE

CROSS-REFERENCE TO RELATED APPLICATION

This application claims priority from Provisional Application No. 61/736,333 filed Dec. 12, 2012, the contents of which are hereby incorporated by reference in its entirety.

FIELD OF THE INVENTION

This invention relates to a new family of aluminosilicate zeolites designated UZM-44 as the catalytic composite for dehydrocyclodimerization reactions. They are represented by the empirical formula of:

$$Na_nM_m^{k+}T_rAl_{1-x}E_xSi_yO_z$$

where M represents a metal or metals from zinc or Group 1 (IUPAC 1), Group 2 (IUPAC 2), Group 3 (IUPAC 3) or the lanthanide series of the periodic table, T is the organic directing agent derived from reactants R and Q where R is an A,Ω-dihalosubstituted alkane such as 1,5-dibromopentane and Q is at least one neutral amine having 6 or fewer carbon atoms such as 1-methylpyrrolidine. E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

A particular zeolite, IM-5, was first disclosed by Benazzi, et al. in 1996 (FR96/12873; WO98/17581) who describe the synthesis of IM-5 from the flexible dicationic structure directing agent, 1,5-bis(N-methylpyrrolidinium)pentane dibromide or 1,6-bis(N-methylpyrrolidinium)hexane dibromide in the presence of sodium. After the structure of IM-5 was solved by Baerlocher et al. (Science, 2007, 315, 113-6), the International Zeolite Structure Commission gave the code of IMF to this zeolite structure type, see Atlas of Zeolite Framework Types. The IMF structure type was found to contain three mutually orthogonal sets of channels in which each channel is defined by a 10-membered ring of tetrahedrally coordinated atoms, however, connectivity in the third dimension is interrupted every 2.5 nm, therefore diffusion is somewhat limited. In addition, multiple different sizes of 10-membered ring channels exist in the structure.

Applicants have successfully prepared a new family of materials designated UZM-44. The topology of the materials is similar to that observed for IM-5. The materials are prepared via the use of a mixture of simple commercially available structure directing agents, such as 1,5-dibromopentane and 1-methylpyrrolidine. UZM-44 may be used as a catalyst in dehydrocyclodimerization reactions where aliphatic hydrocarbons containing from 2 to 6 carbon atoms per molecule are reacted over a catalyst to produce a high yield of aromatics and hydrogen, with a light ends byproduct and a $C_2$-$C_4$ recycle product. Processes for dehydrocyclodimerization are known and described in detail in U.S. Pat. No. 4,654,455 and U.S. Pat. No. 4,746,763 which are incorporated by reference.

SUMMARY OF THE INVENTION

As stated, the present invention relates to using a new catalytic composite comprising a new aluminosilicate zeolite designated UZM-44 in a process for dehydrocyclodimerization. Accordingly, one embodiment of the invention uses a material having a three-dimensional framework of at least $AlO_2$ and $SiO_2$ tetrahedral units and an empirical composition in the as synthesized and anhydrous basis expressed by an empirical formula of:

$$Na_nM_m^{k+}T_rAl_{1-x}E_xSi_yO_z$$

where "n" is the mole ratio of Na to (Al+E) and has a value from approximately 0.05 to 0.5, M represents at least one metal selected from the group consisting of zinc, Group 1 (IUPAC 1), Group 2 (IUPAC 2), Group 3 (IUPAC 3), and the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from about 0.5 to about 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+40 \cdot y)/2$$

and the zeolite is characterized in that it has the x-ray diffraction pattern having at least the d-spacings and intensities set forth in Table A. The zeolite is thermally stable up to a temperature of greater than 600° C. in one embodiment and at least 800° C. in another embodiment.

Another embodiment is directed to the dehydrocyclodimerization process using a second microporous crystalline zeolite, UZM-44-Modified, which has a three-dimensional framework of at least $AlO_2$ and $SiO_2$ tetrahedral units and an empirical composition in the hydrogen form expressed by an empirical formula of $$M1_a^{N+}Al_{(1-x)}E_xSi_yO_{z''}$$

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

The zeolite may be characterized in that it has the x-ray diffraction pattern having at least the d-spacings and intensities set forth in Table B. The zeolite is thermally stable up to a temperature of greater than 600° C. in one embodiment and at least 800° C. in another embodiment.

The zeolite of the catalytic composite used in the process may be prepared by a process comprising forming a reaction mixture containing reactive sources of Na, R, Q, Al, Si and optionally E and/or M and heating the reaction mixture at a temperature of about 160° C. to about 180° C., or about 165° C. to about 175° C., for a time sufficient to form the zeolite. The reaction mixture has a composition expressed in terms of mole ratios of the oxides of:

$$a\text{-}b\text{Na}_2\text{O}:b\text{M}_{n/2}\text{O}:c\text{RO}:d\text{Q}:1\text{-}e\text{Al}_2\text{O}_3:e\text{E}_2\text{O}_3:\\f\text{SiO}_2:g\text{H}_2\text{O}$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. With this number of reactive reagent sources, many orders of addition can be envisioned. Typically, the aluminum reagent is dissolved in the sodium hydroxide prior to adding the silica reagents. Reagents R and Q can be added together or separately in many different orders of addition.

The invention uses UZM-44 as the catalyst or a catalyst component in a process of dehydrocyclodimerization using the above-described zeolite as at least a portion of the catalytic composite. The process comprises reacting aliphatic hydrocarbons containing from 2 to about 6 carbon atoms per molecule over a catalyst to produce a high yield of aromatics and hydrogen, with a light ends byproduct and a $C_2$-$C_4$ recycle product. The dehydrocyclodimerization reaction is carried out at temperatures in excess of 300° C. (572° F.), using the dual functional catalyst containing acidic and dehydrogenation components. At least the acidic function is provided by the zeolite described above which promotes the oligomerization and aromatization reactions. Optionally, a non-noble metal component may also be used to promote the dehydrogenation function.

DETAILED DESCRIPTION OF THE INVENTION

Figure 1:
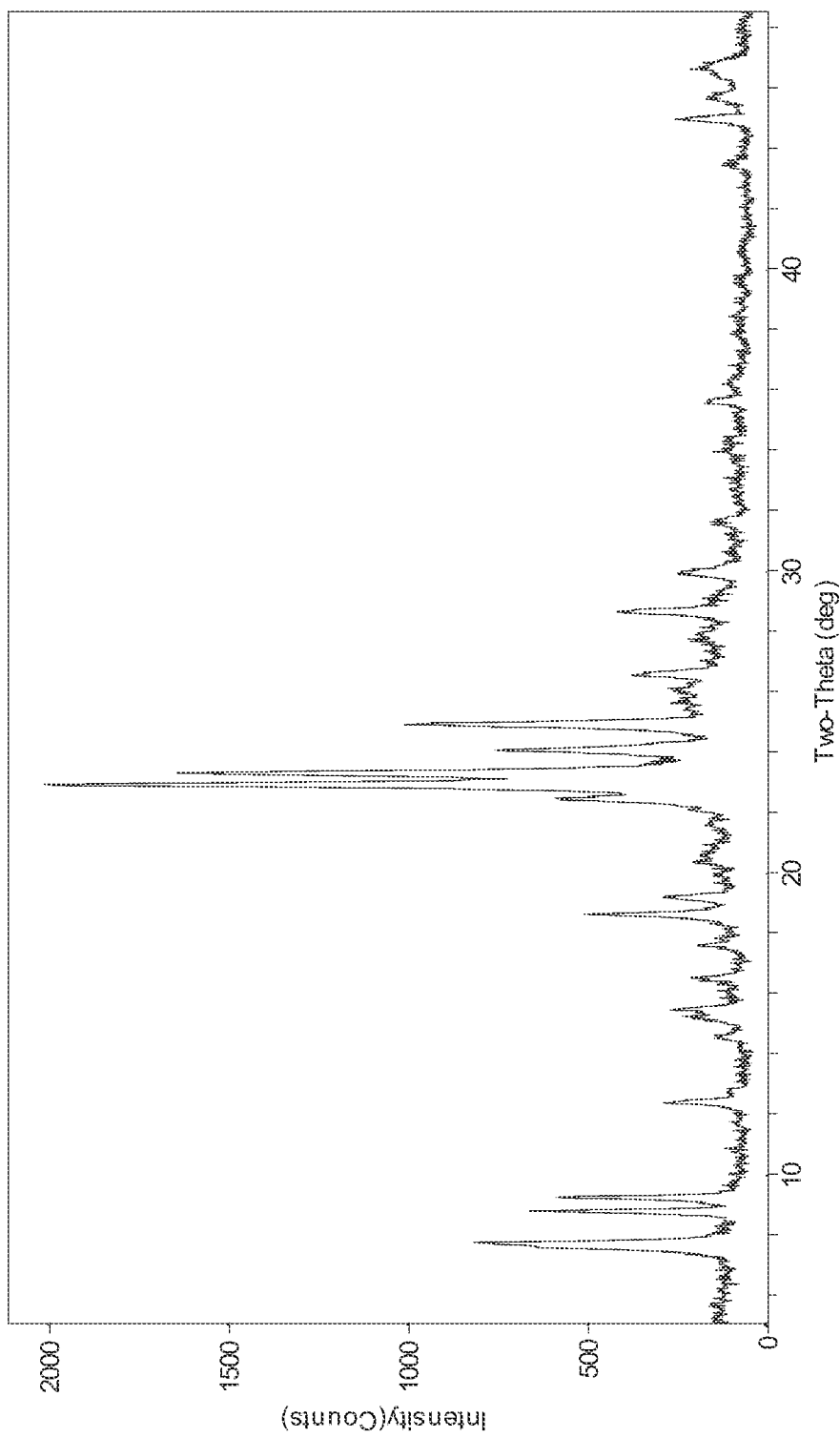
FIG. 1 is an XRD pattern of the UZM-44 zeolite formed in Example 1. This pattern shows the UZM-44 zeolite in the as-synthesized form.
Figure 2:
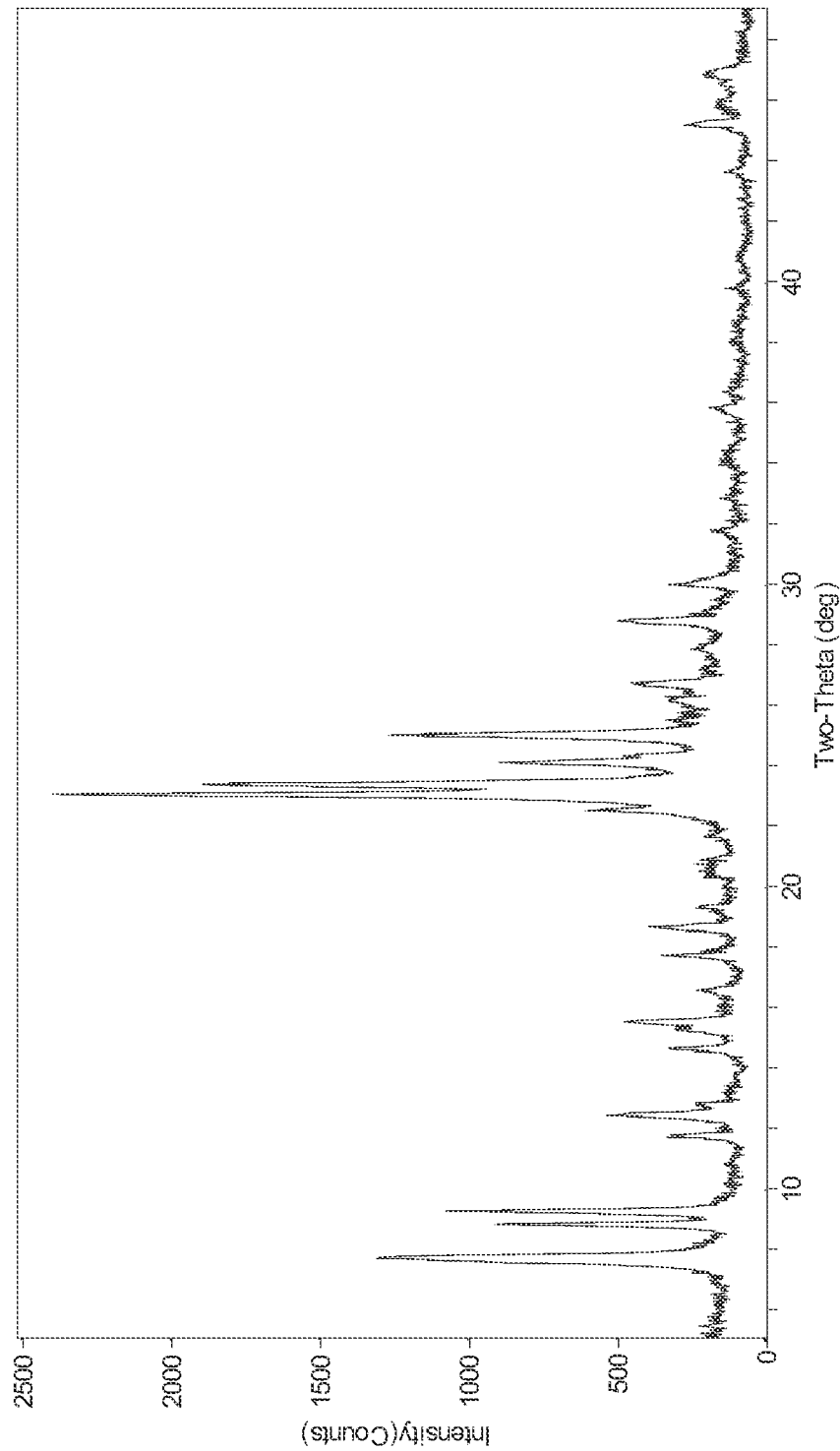
FIG. 2 is also an XRD pattern of the UZM-44 zeolite formed in Example 1. This pattern shows the UZM-44 zeolite in the H$^+$ form.

Applicants have prepared a catalytic component suitable for catalyzing dehydrocyclodimerization reactions where the catalytic component is an aluminosilicate zeolite whose topological structure is related to IMF as described in Atlas of Zeolite Framework Types, which is maintained by the International Zeolite Association Structure Commission at http://www.iza-structure.org/databases/, the member of which has been designated IM-5. As will be shown in detail, UZM-44 is different from IM-5 in a number of its characteristics including its micropore volume. The instant microporous crystalline zeolite, UZM-44, has an empirical composition in the as synthesized and anhydrous basis expressed by an empirical formula of:

$$\text{Na}_n\text{M}_m^{k+}\text{T}_t\text{Al}_{1-x}\text{E}_x\text{Si}_y\text{O}_z$$

where "n" is the mole ratio of Na to (Al+E) and has a value from approximately 0.05 to 0.5, M represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

where M is only one metal, then the weighted average valence is the valence of that one metal, i.e. +1 or +2. However, when more than one M metal is present, the total amount of:

$$M_m^{k+}=M_{m1}^{(k1)+}+M_{m2}^{(k2)+}+M_{m3}^{(k3)+}+M_{m4}^{(k4)+}+\ldots$$

and the weighted average valence "k" is given by the equation:

$$k = \frac{m1 \cdot k1 + m2 \cdot k2 + m3 \cdot k3 \ldots}{m1 + m2 + m3 \ldots}$$

In one embodiment, the microporous crystalline zeolite, UZM-44, is synthesized by a hydrothermal crystallization of a reaction mixture prepared by combining reactive sources of sodium, organic structure directing agent or agents T, aluminum, silicon, and optionally E, M, or both. The reaction mixture does not comprise seeds of a layered material L. The sources of aluminum include but are not limited to aluminum alkoxides, precipitated aluminas, aluminum metal, aluminum hydroxide, sodium aluminate, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, precipitated silica and alkali silicates. Sources of sodium include but are not limited to sodium hydroxide, sodium bromide, sodium aluminate, and sodium silicate.

T is the organic structure directing agent or agents derived from reactants R and Q where R is an A,Ω-dihalogen substituted alkane having 5 carbon atoms and Q comprises at least one neutral monoamine having 6 or fewer carbon atoms. R may be an AS2-dihalogen substituted alkane having 5 carbon atoms selected from the group consisting of 1,5-dichloropentane, 1,5-dibromopentane, 1,5-diiodopentane, and combinations thereof. Q comprises at least one neutral monoamine having 6 or fewer carbon atoms such as 1-ethylpyrrolidine, 1-methylpyrrolidine, 1-ethylazetidine, 1-methylazetidine, triethylamine, diethylmethylamine, dimethylethylamine, trimethylamine, dimethylbutylamine, dimethylpropylamine, dimethylisopropylamine, methylethylpropylamine, methylethylisopropylamine, dipropylamine, diisopropylamine, cyclopentylamine, methylcyclopentylamine, hexamethyleneimine. Q may comprise combinations of multiple neutral monoamines having 6 or fewer carbon atoms.

M represents at least one exchangeable cation of a metal or metals from Group 1 (IUPAC 1), Group 2 (IUPAC 2), Group 3 (IUPAC 3) or the lanthanide series of the periodic table and or zinc. Specific examples of M include but are not limited to lithium, potassium, rubidium, cesium, magnesium, calcium, strontium, barium, zinc, yttrium, lanthanum, gadolinium, and mixtures thereof. Reactive sources of M include, but are not limited to, the group consisting of halide, nitrate, sulfate, hydroxide, or acetate salts. E is an element selected from the group consisting of gallium, iron, boron and combinations thereof, and suitable reactive sources include, but are not limited to, boric acid, gallium oxyhydroxide, gallium nitrate, gallium sulfate, ferric nitrate, ferric sulfate, ferric chloride and mixtures thereof.

The reaction mixture containing reactive sources of the desired components can be described in terms of molar ratios of the oxides by the formula:

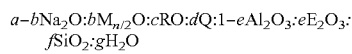

$$a\text{--}b\text{Na}_2\text{O}:b\text{M}_{n/2}\text{O}:c\text{RO}:d\text{Q}:1\text{--}e\text{Al}_2\text{O}_3:e\text{E}_2\text{O}_3: f\text{SiO}_2:g\text{H}_2\text{O}$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. The examples demonstrate specific orders of addition for the reaction mixture which leads to UZM-44. However, as there are at least 6 starting materials, many orders of addition are possible. Also, if alkoxides are used, it is preferred to include a distillation or evaporative step to remove the alcohol hydrolysis products. While the organic structure directing agents R and Q can be added separately or together to the reaction mixture at a number of points in the process, it is preferred to mix R and Q together at room temperature and add the combined mixture to a cooled mixture of reactive Si, Al and Na sources maintained at 0-10° C. Alternatively, the mixture of R and Q, after mixing at room temperature, could be cooled and the reactive sources of Si, Al, and Na added to the organic structure directing agent mixture while maintaining a temperature of 0-10° C. In an alternative embodiment, the reagents R and Q could be added, separately or together, to the reaction mixture at room temperature.

The reaction mixture is then reacted at a temperature of about 160° C. to about 180° C., or about 165° C. to about 175° C., for a period of about 1 day to about 3 weeks and preferably for a time of about 3 days to about 14 days in a stirred, sealed reaction vessel under autogenous pressure. Static crystallization does not yield UZM-44. After crystallization is complete, the solid product is isolated from the heterogeneous mixture by means such as filtration or centrifugation, and then washed with deionized water and dried in air at ambient temperature up to about 100° C.

The as-synthesized UZM-44 is characterized by the x-ray diffraction pattern, having at least the d-spacings and relative intensities set forth in Table A below. Diffraction patterns herein were obtained using a typical laboratory powder diffractometer, utilizing the $K_\alpha$ line of copper; Cu K alpha. From the position of the diffraction peaks represented by the angle 2theta, the characteristic interplanar distances $d_{hkl}$ of the sample can be calculated using the Bragg equation. The intensity is calculated on the basis of a relative intensity scale attributing a value of 100 to the line representing the strongest peak on the X-ray diffraction pattern, and then: very weak (vw) means less than 5; weak (w) means less than 15; medium (m) means in the range 15 to 50; strong (s) means in the range 50 to 80; very strong (vs) means more than 80. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular coherently grown composite structures or for samples with crystals which are small enough to cause significant broadening of the X-rays. This can also be the case when the equipment or operating conditions used to produce the diffraction pattern differ significantly from those used in the present case.

The X-ray diffraction pattern for UZM-44 contains many peaks, an example of the x-ray diffraction patterns for an as-synthesized UZM-44 product is shown in FIG. 1. Those peaks characteristic of UZM-44 are shown in Table A. Additional peaks, particularly those of very weak intensity, may also be present. All peaks of medium or higher intensity present in UZM-44 are represented in Table A.

The zeolite may be further characterized by the x-ray diffraction pattern having at least the d-spacings and intensities set forth in Table A.

TABLE A

| 2-Theta | d(Å) | I/Io % |
|---|---|---|
| 7.72 | 11.45 | m |
| 8.88 | 9.95 | m |
| 9.33 | 9.47 | m |
| 12.47 | 7.09 | w-m |
| 12.85 | 6.88 | vw |
| 14.62 | 6.05 | vw-w |
| 15.27 | 5.80 | w |
| 15.57 | 5.68 | w |
| 16.60 | 5.34 | w |
| 17.70 | 5.01 | vw-w |
| 18.71 | 4.74 | w-m |
| 19.30 | 4.59 | w |
| 22.55 | 3.94 | m |
| 23.03 | 3.86 | vs |
| 23.39 | 3.80 | s |
| 24.17 | 3.68 | m |
| 25.01 | 3.56 | m |
| 26.19 | 3.40 | vw-w |
| 26.68 | 3.34 | w-m |
| 28.76 | 3.10 | w-m |
| 30.07 | 2.97 | w |
| 35.72 | 2.51 | vw-w |
| 45.08 | 2.01 | w |
| 45.83 | 1.98 | vw-w |
| 46.77 | 1.94 | vw-w |

As will be shown in detail in the examples, the UZM-44 material is thermally stable up to a temperature of at least 600° C. and in another embodiment, up to at least 800° C. Also as shown in the examples, the UZM-44 material may have a micropore volume as a percentage of total pore volume of less than 60%.

Characterization of the UZM-44 product by high-resolution scanning electron microscopy shows that the UZM-44 forms in lathes which assemble into rectangular rod colonies.

As synthesized, the UZM-44 material will contain some exchangeable or charge balancing cations in its pores. These exchangeable cations can be exchanged for other cations, or in the case of organic cations, they can be removed by heating under controlled conditions. It is also possible to remove some organic cations from the UZM-44 zeolite directly by ion exchange. The UZM-44 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination, ion-exchange and calcination and on an anhydrous basis, the microporous crystalline zeolite UZM-44 has a three-dimensional framework of at least $AlO_2$ and $SiO_2$ tetrahedral units and an empirical composition in the hydrogen form expressed by an empirical formula of

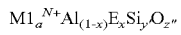

$$M1_a^{N+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

In the hydrogen form, after calcination, ion-exchange and calcination to remove $NH_3$, UZM-44 displays the x-ray diffraction pattern having at least the d-spacings and intensities set forth in Table B. Those peaks characteristic of UZM-44 are shown in Tables B. Additional peaks, particularly those of very weak intensity, may also be present. All peaks of medium or higher intensity present in UZM-44 in Table B.

TABLE B

| 2-Theta | d(Å) | I/Io % |
|---|---|---|
| 7.71 | 11.47 | m-s |
| 8.84 | 10.00 | m-s |
| 9.24 | 9.56 | m |
| 11.76 | 7.52 | vw-w |
| 12.46 | 7.10 | m |
| 14.38 | 6.15 | vw |
| 14.64 | 6.05 | w |
| 15.26 | 5.80 | w |
| 15.52 | 5.70 | w-m |
| 16.58 | 5.34 | w |
| 17.72 | 5.00 | w-m |
| 18.64 | 4.76 | w |
| 22.56 | 3.94 | w-m |
| 23.06 | 3.85 | vs |
| 23.40 | 3.80 | s |
| 24.12 | 3.69 | m |
| 25.06 | 3.55 | m |
| 26.16 | 3.40 | vw-w |
| 26.74 | 3.33 | w-m |
| 28.82 | 3.10 | w-m |
| 30.12 | 2.96 | w |
| 35.86 | 2.50 | vw-w |

TABLE B-continued

| 2-Theta | d(Å) | I/Io % |
|---|---|---|
| 45.32 | 2.00 | w |
| 46.05 | 1.97 | vw-w |
| 46.92 | 1.93 | vw-w |

Similar to the as-synthesized material, the modified UZM-44 materials are thermally stable up to a temperature of at least 600° C. and in another embodiment, up to at least 800° C. and may have a micropore volume as a percentage of total pore volume of less than 60%.

Figure 3:
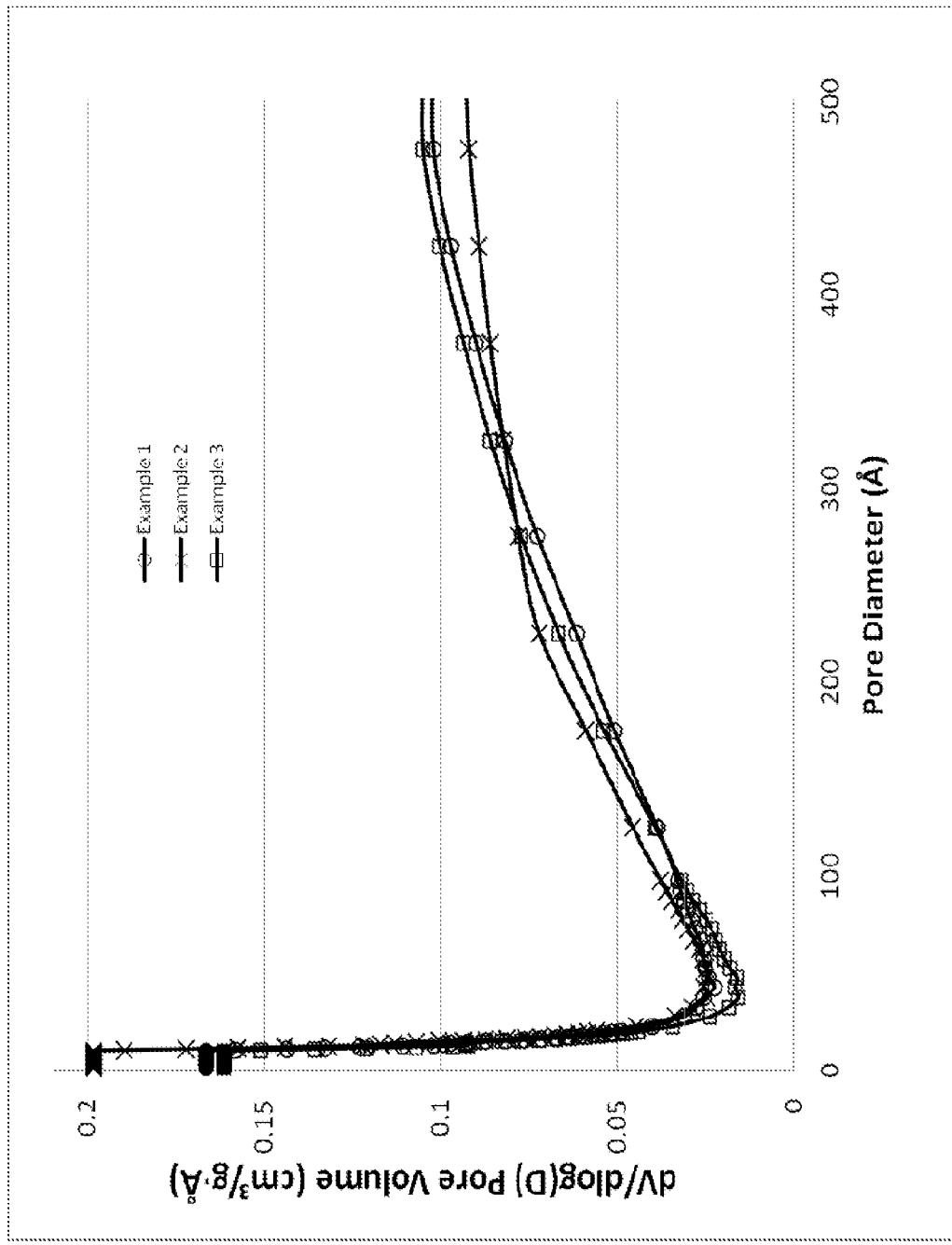
FIG. 3 is a plot derived from the N2 BET experiment where dV/dlog(D) is plotted against the pore diameter. This plot shows the incremental amount of nitrogen adsorbed at each pore diameter measured.

Surface area, micropore volume and total pore volume may be determined, for example, by $N_2$ adsorption using the conventional BET method of analysis (J. Am. Chem. Soc., 1938, 60, 309-16) coupled with t-plot analysis of the adsorption isotherm as implemented in Micromeritics ASAP 2010 software. The t-plot is a mathematical representation of multilayer adsorption and allows determination of the amount of $N_2$ adsorbed in the micropores of the zeolitic material under analysis. In particular, for the materials described herein, points at 0.45, 0.50, 0.55, 0.60, and 0.65 $P/P_0$ are used to determine the slope of the t-plot line, the intercept of which is the micropore volume. Total pore volume is determined at 0.98 $P/P_0$. The UZM-44 of the instant invention has a micropore volume of less than 0.155 mL/g, typically less than 0.15 and often less than 0.145 mL/g. Additionally, by looking at the dV/dlog D versus pore diameter plot (the differential volume of nitrogen adsorbed as a function of pore diameter), as shown in FIG. 3, the UZM-44 of the instant invention contains no feature at around 200-300 Å, where the Example 2 material does and instead have adsorption occurring at greater than 450 Å, where greater than 0.1 mL $N_2$/gÅ is differentially adsorbed at a pore diameter of 475 Å. Preferably, greater than 0.1 mL $N_2$/gÅ is differentially adsorbed at a pore diameters greater than 475 Å where differentially adsorbed indicates the differential volume of nitrogen adsorbed at a particular pore diameter.

By virtually pure silica is meant that virtually all the aluminum and/or the E metals have been removed from the framework. It is well known that it is virtually impossible to remove all the aluminum and/or E metal. Numerically, a zeolite is virtually pure silica when y' has a value of at least 3,000, preferably 10,000 and most preferably 20,000. Thus, ranges for y' are from 9 to 3,000; from greater than 20 to about 3,000; from 9 to 10,000; from greater than 20 to about 10,000; from 9 to 20,000; and from greater than 20 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The UZM-44 zeolite is employed as at least a portion of a catalyst in a dehydrocyclodimerization process for preparing an aromatic stream from a light aliphatic hydrocarbon stream. The process uses a dehydrocyclodimerization catalyst which comprises the UZM-44 zeolite component, optionally a binder component, and optionally a metal component. The metal component may be a metal such as gallium to promote the dehydrogenation function. The gallium component may be incorporated into the catalytic composite in any suitable manner known to the art which results in a uniform dispersion of the gallium such as by ion-exchange, cogelation, or impregnation either after, before, or during the compositing of the catalyst formulation. Usually the gallium is deposited onto the catalyst by impregnating the catalyst with a salt of the gallium metal. The particles are impregnated with using gallium metal or gallium containing compounds such as gallium oxyhydroxide, gallium nitrate, gallium chloride, gallium bromide, gallium sulfate, gallium acetate, and gallium oxide. The amount of gallium which is deposited onto the catalyst varies from about 0.1 to about 5 weight percent of the finished catalyst expressed as the metal. The gallium compound may be impregnated onto the support particles by any technique well known in the art such as dipping the catalyst into a solution of the metal compound or spraying the solution onto the support. One method of preparation involves the use of a steam jacketed rotary dryer. The support particles are immersed in the impregnating solution contained in the dryer and the support particles are tumbled therein by the rotating motion of the dryer. Evaporation of the solution in contact with the tumbling support is expedited by applying steam to the dryer jacket. Following drying, the gallium impregnated catalyst may then be calcined to convert the gallium to the oxide phase. An exemplary method for performing the gallium incorporation step is disclosed in U.S. Pat. No. 6,657,096, hereby incorporated by reference.

The zeolite as outlined above, or a modification thereof, may be in a composite with commonly known binders. The UZM-44 is used as a catalyst or catalyst support in various reactions. The UZM-44 preferably is mixed with a binder for convenient formation of catalyst particles in a proportion of about 5 to 100 mass % UZM-44 zeolite and 0 to 95 mass-% binder, with the UZM-44 zeolite preferably comprising from about 10 to 90 mass-% of the composite. The binder should preferably be porous, have a surface area of about 5 to about 800 m$^2$/g, and be relatively refractory to the conditions utilized in the hydrocarbon conversion process. Non-limiting examples of binders are alumina, titania, zirconia, zinc oxide, magnesia, boria, silica-alumina, silica-magnesia, chromia-alumina, alumina-boria, aluminophosphates, silica-zirconia, silica, silica gel, and clays. Preferred binders are aluminophosphates, amorphous silica and alumina, including gamma-, eta-, and theta-alumina, with aluminophosphates being especially preferred.

The zeolite with or without a binder can be formed into various shapes such as pills, pellets, extrudates, spheres, etc. Preferred shapes are extrudates and spheres. Extrudates are prepared by conventional means which involves mixing of the composition either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50 to about 200° C. and subjected to a calcination procedure at a temperature of about 450 to about 700° C. for a period of about 1 to about 20 hours. This treatment effects conversion of the hydrogel to the corresponding oxide or phosphate matrix.

The dehydrocyclodimerization conditions which are employed vary depending on such factors as feedstock composition and desired conversion. A desired range of conditions for the dehydrocyclodimerization of $C_2$-$C_6$ aliphatic hydrocarbons to aromatics include a temperature from about 350° C. to about 650° C. (662° F. to 1202° F.), a pressure from about 0 to about 300 psi(g) (0 to 2068 kPa(g)), and a liquid hourly space velocity from about 0.2 to about 5 hr$^{-1}$. One embodiment of the invention employs process conditions including a temperature in the range from about 400° C. to about 600° C. (752° F. to 1112° F.), a pressure in or about the range from about 0 to about 150 psi(g) (0 to 1034 kPa(g)), and a liquid hourly space velocity of between 0.5 to 3.0 hr$^{-1}$. It is understood that, as the average carbon number of the feed increases, a temperature in the lower end of the temperature range is required for optimum performance and conversely, as the average carbon number of the feed decreases, the higher the required temperature.

The feed stream to the dehydrocyclodimerization process is defined herein as all streams introduced into the dehydrocyclodimerization reaction zone. Included in the feed stream is the at least one aliphatic hydrocarbon having from 2 to about 6 carbon atoms. The feed stream is referred to as comprising $C_2$-$C_6$ aliphatic hydrocarbons. By $C_2$-$C_6$ aliphatic hydrocarbons is meant one or more open, straight or branched chain isomers having from two to six carbon atoms per molecule. Furthermore, the hydrocarbons in the feedstock may be saturated or unsaturated. Preferably, the hydrocarbons are $C_3$'s and/or $C_4$'s selected from isobutane, normal butane, isobutene, normal butene, propane and propylene. Examples of potential feed streams include $C_3$ and/or $C_4$ derived streams from FCC cracked products, light gasses from a delayed coking process, and liquefied petroleum gas streams (LPG). Diluents may also be included in the feed stream. Examples of such diluents include water, nitrogen, helium, argon, neon. Aromatic products generated by the dehydrocyclodimerization process may include benzene, toluene, xylenes, aromatics with 9 or 10 carbon atoms, and mixtures thereof. In one embodiment, the aromatic products include benzene, toluene, and xylenes. The aromatic products may be used as reactants in later refining or petrochemical processes.

Molecular hydrogen is produced in a dehydrocyclodimerization reaction as well as aromatic hydrocarbons. For example, reacting a $C_4$ paraffin will yield 5 moles of hydrogen for every one mole of aromatic produced. Because the equilibrium concentration of aromatics is inversely proportional to the fifth power of the hydrogen concentration, it is desired to carry out the reaction in the absence of added hydrogen. Adherence to this practice, however, promotes catalyst deactivation and, as a result, short catalyst life before regeneration. The rapid deactivation is believed to be caused by excessive carbon formation (coking) on the catalyst surface. This coking tendency makes it necessary to relatively frequently perform catalyst regeneration. Reducing the deactivation occurring during successive regenerations requires a hydrothermally stable zeolite, that is, a zeolite for which surface area, micropore volume and/or tetrahedral Al content are stable after exposure to high temperatures and steam quantities. The catalyst used in this dehydrocyclodimerization has the advantage of hydrothermal stability which may lead to longer catalyst life.

The catalyst may be in a fixed bed system, a moving bed system, a fluidized bed system, or in a batch type operation; however, in view of the danger of attrition losses of the valuable catalyst and of the well-known operational advantages, it is preferred to use either a fixed bed system or a dense-phase moving bed system.

In a fixed bed system or a dense-phase moving bed system, the feed stream is preheated by any suitable heating means to the desired reaction temperature and then passed into a dehydrocyclodimerization zone containing a bed of catalyst. It is understood that the dehydrocyclodimerization zone may be one or more separate reactors with suitable means between separate reactors if any to compensate for any endothermicity encountered in each reactor and to assure that the desired temperature is maintained at the entrance to each reactor. It is also important to note that the feed stream may be contacted with the catalyst bed in either upward, downward, or radial flow fashion with the latter being preferred. In addition, the feed stream is in the vapor phase when its' components contact the catalyst bed. Each reactor may contain one or more fixed or dense-phase moving beds of catalyst.

The dehydrocyclodimerization system may comprise a dehydrocyclodimerization zone containing one or more reactors and/or beds of catalyst. In a multiple bed system, it is, of course, within the scope of the present invention to use one catalyst in less than all of the beds with another dehydrocyclodimerization or similarly behaving catalyst being used in the remainder of the beds. Specific to the dense-phase moving bed system, it is common practice to remove catalyst from the bottom of a reactor in the dehydrocyclodimerization zone, regenerate it by conventional means known to the art, and then return it to the top of that reactor or another reactor in the dehydrocyclodimerization zone. The reactor or reactors utilized in the process may be linked to a product recovery system in various manners described in the prior art to achieve specific desired results. U.S. Pat. No. 4,642,402 for example discloses a method of combining a reaction zone and product recovery zone to optimize the xylene produced in a dehydrocyclodimerization process. The product recovery section may recover streams such as hydrogen, light hydrocarbons, and benzene. In an embodiment, at least a portion of a light hydrocarbon stream comprising $C_2$-$C_6$ hydrocarbons is recycled to the dehydrocyclodimerization zone as a portion of the feedstream. In another an embodiment, at least a portion of the benzene stream is recycled to the dehydrocyclodimerization zone as a portion of the feedstream After some time on stream (several days to a year), the catalyst described above will have lost enough activity due to coking and hydrogen exposure so that it must be reactivated. It is believed that the exact amount of time which a catalyst can operate without necessitating regeneration or reactivation will depend on a number of factors. One factor, as is demonstrated herein is whether water is added to the feed stream.

When the catalyst requires regeneration, typically oxidation or burning of catalyst deactivating carbonaceous deposits with oxygen or an oxygen-containing gas is used. Catalyst regeneration techniques are well known and not discussed in detail here. Examples include U.S. Pat. No. 4,795,845 (hereby incorporated by reference) which discloses burning the coke accumulated upon the deactivated catalyst at catalyst regeneration conditions in the presence of an oxygen-containing gas, and U.S. Pat. No. 4,724,271 (hereby incorporated by reference) which additionally discloses water removal steps in the catalyst regeneration procedure. The regeneration may proceed in one or multiple burns. For example, there may be a main burn followed by a clean-up burn. The main burn constitutes the principal portion of the regeneration process with the clean-up burn gradually increasing the amount of molecular oxygen in the gas introduced to the regeneration catalyst until the end of the clean-up burn which is indicated by a gradual decline in the temperature at the edit of the catalyst bed until the inlet and outlet temperatures of the catalyst bed merges.

In addition to deactivation by coking requiring regeneration, dehydrocyclodimerization catalysts can be deactivated by exposure to hydrogen at high temperatures and then require reactivation. Similarly, when the catalyst requires reactivation, it is removed from the operating reactor and contacted with fluid water. Suitable reactivation processes are known and not discussed in detail here. One example is U.S. Pat. No. 6,395,664. Using procedures in the art, the catalyst can be reactivated multiple times. Thus, the catalyst can be hydrogen deactivated, then reactivated, then hydrogen deactivated again, then reactivated again and so forth. No limit on the number of times that a particular catalyst can be deactivated and subsequently reactivated is known. The application and use of additional required items are well within the purview of a person of ordinary skill in the art. U.S. Pat. No. 3,652,231; U.S. Pat. No. 3,647,680; and U.S. Pat. No. 3,692,496; which are incorporated by reference into this document, may be consulted for additional detailed information.

The following examples are presented in illustration of this invention and are not intended as undue limitations on the generally broad scope of the invention as set out in the appended claims.

The structure of the UZM-44 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, w and vw which represent very strong, strong, medium, weak, and very weak respectively. In terms of 100×I/$I_o$, the above designations are defined as:

$$vw=<5; w=6-15; m=16-50; s=51-80; \text{ and } vs=80-100$$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

5.28 g of NaOH, (97%) was dissolved in 111.88 g water. 1.16 g Al(OH)$_3$, (29.32 wt.-% Al), was added to the sodium hydroxide solution. Upon the mixture becoming a solution, 33.75 g Ludox AS-40 was added and the solution was stirred vigorously for 1-2 hours and then cooled to 0° C.-4° C. Separately, 8.89 g 1,5-dibromopentane, (97%) was mixed with 9.56 g 1-methylpyrrolidine, (97%) to form a second mixture. The second mixture was added to the cooled mixture to create the final reaction mixture. The final reaction mixture was vigorously stirred and transferred to a 300 cc stirred autoclave. The final reaction mixture was digested at 170° C. for 120 hours with stirring at 100 rpm. The product was isolated by filtration. The product was identified as UZM-44 by XRD. Analytical results showed this material to have the following molar ratios, Si/Al of 11.77, Na/Al of 0.21, N/Al of 1.02, C/N of 7.75. The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged ample shows 39.1% Si, 3.26% Al, 90 ppm Na with a BET surface area of 299 m$^2$/g, pore volume of 0.239 cm3/g, and micropore volume of 0.139 cm3/g.

Comparative Example 2

10.8 g of Aerosil 200 was added, while stirring, to a solution of 12.24 g 1,5-bis(N-methylpyrrolidinium)pentane dibromide in 114 g H$_2$O. A very thick gel was formed. Separately, a solution was made from 60 g H$_2$O, 3.69 g NaOH (99%), 0.95 g sodium aluminate (26.1% Al by analysis), and 1.86 g NaBr (99%). This second solution was added to the above mixture. The final mixture was divided equally between 7 45 cc Parr vessels. One vessel, which was digested for 12 days at 170° C. in a rotisserie oven at 15 rpm, yielded a product which was determined by XRD as having the IMF structure. The product was isolated by filtration. Analytical results showed this material to have the following molar ratios, Si/Al of 12.12, Na/Al of 0.08, N/Al of 1.03, C/N of 7.43. The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 38.8% Si, 2.99% Al, 190 ppm Na with a BET surface area of 340 m$^2$/g, pore volume of 0.260 cm$^3$/g, and micropore volume of 0.160 cm$^3$/g.

Example 3

The final reaction mixture was vigorously stirred and transferred to a 5 gallon stirred autoclave. The product was isolated by filtration. The product was identified as UZM-44 by XRD. Analytical results showed this material to have the following molar ratios, Si/Al of 11.77, Na/Al of 0.21, N/Al of 1.02, C/N of 7.75. The product generated by this synthesis was calcined under flowing air at 600° for 6 hours. Analysis for the calcined sample shows a BET surface area of 301 m$^2$/g, pore volume of 0.238 cm$^3$/g, and micropore volume of 0.142 cm$^3$/g.

Example 4

A UZM-44 in the H+ form was loaded into a vertical steamer. The UZM-44 was exposed to 100% steam at 725° C. for 12 hours or 24 hours. The starting UZM-44 had a BET surface area of 340 m$^2$/g, pore volume of 0.301 cm$^3$/g, and micropore volume of 0.154 cm$^3$/g. After 12 hours of steaming, the UZM-44 was still identified as UZM-44 by XRD though the intensity of the first 3 peaks had increased to very strong, very strong—strong, and very strong—strong respectively. All other peaks were at positions and intensities described in Table B. The material had a BET surface area of 274 m$^2$/g, pore volume of 0.257 cm$^3$/g, and micropore volume of 0.127 cm$^3$/g. After 24 hours of steaming, the UZM-44 was still identified as UZM-44 by XRD though the intensity of the first 3 peaks had increased to very strong, very strong—strong, and very strong—strong respectively. All other peaks were at positions and intensities described in Table B. The material had a BET surface area of 276 m$^2$/g, pore volume of 0.262 cm$^3$/g, and micropore volume of 0.128 cm$^3$/g. The UZM-44 demonstrated high hydrothermal stability.

Example 5

The product generated by the synthesis described in Example 1 was bound with Al$_2$O$_3$ in a 75:25 weight ratio and extruded in ⅛" cylinders to form UZM-44/Al$_2$O$_3$. The extrudates were then calcined using a 2° C./minute ramp to 550° C., holding for 3 hours and then cooling to room temperature. The 20 to 60 mesh fraction was isolated and then used as the catalytic composite in a chemical reaction to form ethylbenzene and xylenes.

Benzene and propane were fed at a 2:1 mole ratio into a reactor at 400 psig along with a hydrogen stream such that the hydrogen to hydrocarbon mole ratio was about 1.0. At 500° C. and 2.5 WHSV, conversion of benzene was 63 wt % and conversion of propane was 90 wt %. Yield of aromatic compounds at these conditions included 25 wt % to toluene, 1 wt % to ethylbenzene, 7 wt % to xylenes and 5 wt % to C9 aromatics.

The invention claimed is:
1. A process for dehydrocyclodimerization comprising contacting a feed comprising at least one aliphatic hydrocarbon having from 2 to about 6 carbon atoms per molecule with a microporous crystalline zeolitic catalytic composite at dehydrocyclodimerization conditions to produce a product stream comprising at least one aromatic hydrocarbon wherein the catalytic composite is selected from the group consisting of
   a. a first microporous crystalline zeolite, UZM-44, having a three-dimensional framework of at least AlO$_2$ and SiO$_2$ tetrahedral units and an empirical composition in the as synthesized and anhydrous basis expressed by an empirical formula of:

$$Na_nM_m^{k+}T_tAl_{1-x}E_xSi_yO_z$$

where "n" is the mole ratio of Na to (Al+E) and has a value from approximately 0.05 to 0.5, M represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

and characterized in that it has the x-ray diffraction pattern having at least the d-spacings and intensities set forth in Table A:

TABLE A

| 2-Theta | d(†) | I/Io % |
|---|---|---|
| 7.72 | 11.45 | m |
| 8.88 | 9.95 | m |
| 9.33 | 9.47 | m |
| 12.47 | 7.09 | w-m |
| 12.85 | 6.88 | vw |
| 14.62 | 6.05 | vw-w |
| 15.27 | 5.80 | w |
| 15.57 | 5.68 | w |
| 16.60 | 5.34 | w |
| 17.70 | 5.01 | vw-w |
| 18.71 | 4.74 | w-m |
| 19.30 | 4.59 | w |
| 22.55 | 3.94 | m |
| 23.03 | 3.86 | vs |
| 23.39 | 3.80 | s |
| 24.17 | 3.68 | m |
| 25.01 | 3.56 | m |
| 26.19 | 3.40 | vw-w |
| 26.68 | 3.34 | w-m |
| 28.76 | 3.10 | w-m |
| 30.07 | 2.97 | w |
| 35.72 | 2.51 | vw-w |
| 45.08 | 2.01 | w |
| 45.83 | 1.98 | vw-w |
| 46.77 | 1.94 | vw-w | b. a second microporous crystalline zeolite, UZM-44-Modified, having a three-dimensional framework of at least $AlO_2$ and $SiO_2$ tetrahedral units and an empirical composition in the hydrogen form expressed by an empirical formula of

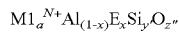

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

and is characterized in that it has the x-ray diffraction pattern having at least the d-spacings and intensities set forth in Table B:

TABLE B

| 2-Theta | d(†) | I/Io % |
|---|---|---|
| 7.71 | 11.47 | m-s |
| 8.84 | 10.00 | m-s |
| 9.24 | 9.56 | m |

TABLE B-continued

| 2-Theta | d(†) | I/Io % |
|---|---|---|
| 11.76 | 7.52 | vw-w |
| 12.46 | 7.10 | m |
| 14.38 | 6.15 | vw |
| 14.64 | 6.05 | w |
| 15.26 | 5.80 | w |
| 15.52 | 5.70 | w-m |
| 16.58 | 5.34 | w |
| 17.72 | 5.00 | w-m |
| 18.64 | 4.76 | w |
| 22.56 | 3.94 | w-m |
| 23.06 | 3.85 | vs |
| 23.40 | 3.80 | s |
| 24.12 | 3.69 | m |
| 25.06 | 3.55 | m |
| 26.16 | 3.40 | vw-w |
| 26.74 | 3.33 | w-m |
| 28.82 | 3.10 | w-m |
| 30.12 | 2.96 | w |
| 35.86 | 2.50 | vw-w |
| 45.32 | 2.00 | w |
| 46.05 | 1.97 | vw-w |
| 46.92 | 1.93 | vw-w | and c. combinations thereof.

2. The process of claim 1 wherein the microporous crystalline zeolitic catalytic composite is thermally stable up to a temperature of greater than 600° C.

3. The process of claim 1 wherein the microporous crystalline zeolitic catalytic composite has a micropore volume as a percentage of total pore volume of less than 60%.

4. The process of claim 1 wherein the microporous crystalline zeolitic catalytic composite has a micropore volume of less than 0.155 mL/g.

5. The process of claim 1 wherein the microporous crystalline zeolitic catalytic composite has a micropore volume of less than 0.150 mL/g.

6. The process of claim 1 wherein the microporous crystalline zeolitic catalytic composite exhibits no feature at 200-300 Å on a dV/dlog D versus pore diameter plot of differential volume of nitrogen adsorbed as a function of pore diameter.

7. The process of claim 1 wherein the microporous crystalline zeolitic catalytic composite exhibits adsorption occurring at greater than 450 Å on a dV/dlog D versus pore diameter plot of differential volume of nitrogen adsorbed as a function of pore diameter.

8. The process of claim 1 wherein the differential volume of nitrogen adsorbed by the zeolite at a pore diameter of 475 Å is greater than 0.1 mL $N_2$/gÅ on a dV/dlog D versus pore diameter plot of differential volume of nitrogen adsorbed as a function of pore diameter.

9. The process of claim 1 wherein the differential volume of nitrogen adsorbed by the zeolite at pore diameters greater than 475 Å is greater than 0.1 mL $N_2$/gÅ on a dV/dlog D versus pore diameter plot of differential volume of nitrogen adsorbed as a function of pore diameter.

10. The process of claim 1 wherein the dehydrocyclodimerization conditions include a temperature from about 350° C. to about 650° C. (662° F. to 1202° F.), a pressure from about 0 to about 300 psi(g) (0 to 2068 kPa(g)), and a liquid hourly space velocity from about 0.2 to about 5 hr$^{-1}$.

11. The process of claim 1 wherein the catalytic composite further comprises gallium and a binder.

12. The process of claim 1 wherein the dehydrocyclodimerization conditions include a temperature in the range from about 400° C. to about 600° C. (752° F. to 1112° F.), a pressure in or about the range from about 0 to about 150 psi(g) (0 to 1034 kPa(g)), and a liquid hourly space velocity of between 0.5 to 3.0 hr$^{-1}$.

13. The process of claim 1 wherein the catalytic composite is located in one or more catalyst zones arranged in series or parallel configuration, and wherein the catalytic composite may be in fixed beds or fluidized beds.

14. The process of claim 1 wherein the at least one aromatic hydrocarbon is benzene, toluene, or a xylene.

15. The process of claim 1 wherein the feed is selected from the group consisting of $C_3$ and/or $C_4$ derived streams from FCC cracked products, light gasses from a delayed coking process, and liquefied petroleum gas streams.

16. The process of claim 1 wherein the process is operated in a fixed bed or dense-phase mode.

17. The process of claim 1 wherein the product stream further comprises light hydrocarbons which are separated from the product stream and recycled to the contacting with a catalytic composite step.

18. The process of claim 1 wherein the product stream comprises benzene and xylenes the process further comprising separating the benzene and recycling the separated benzene to the contacting with a catalytic composite step.

\* \* \* \* \*